US012806412B2

(12) United States Patent
Swoyer et al.

(10) Patent No.: US 12,806,412 B2
(45) Date of Patent: Nov. 24, 2026

(54) LEAD FOR THE TEMPORARY STIMULATION OF A PERIPHERAL NERVE

(71) Applicant: Nextern Innovation, LLC, White Bear Lake, MN (US)

(72) Inventors: John Swoyer, Blaine, MN (US); Jonathan Lawson, Cottage Grove, MN (US); Jesse Geroy, Ham Lake, MN (US); Michael Brenzel, White Bear Lake, MN (US)

(73) Assignee: NEXTERN INNOVATION, LLC, White Bear Lake, MN (US)

( * ) Notice: Subject to any disclaimer, the term of this patent is extended or adjusted under 35 U.S.C. 154(b) by 209 days.

(21) Appl. No.: 18/529,994

(22) Filed: Dec. 5, 2023

(65) Prior Publication Data

US 2024/0216675 A1 Jul. 4, 2024

Related U.S. Application Data

(63) Continuation-in-part of application No. 17/816,645, filed on Aug. 1, 2022, now Pat. No. 11,883,651,
(Continued)

(51) Int. Cl.
*A61N 1/36* (2006.01)
*A61B 17/34* (2006.01)
(Continued)

(52) U.S. Cl.
CPC ........ *A61N 1/0558* (2013.01); *A61B 17/3468* (2013.01); *A61N 1/36017* (2013.01); *A61N 1/3605* (2013.01); *A61N 1/37518* (2017.08)

(58) Field of Classification Search
CPC ... A61N 1/0551; A61N 1/0558; A61N 1/3605
See application file for complete search history.

(56) References Cited

U.S. PATENT DOCUMENTS 3,724,467 A * 4/1973 Avery .................. A61N 1/0551
607/117
5,366,493 A 11/1994 Scheiner et al.
(Continued)

FOREIGN PATENT DOCUMENTS

EP 2914334 B1 8/2019
WO 2009135080 A1 11/2009

OTHER PUBLICATIONS

Daly, et al, Performance of an intramuscular electrode during functional neuromuscular stimulation for gait training post stroke, Journal of Rehabilitation Research & Development, vol. 38 , retrieved online on Jan. 22, 2020 from https://www.rehab.research.va.gov/jour/01/38/5/daly.htm, pp. 513-526, 17 pages, published on 2001.
(Continued)

*Primary Examiner* — Eric D. Bertram
(74) *Attorney, Agent, or Firm* — Definitive Patents, member Synchrony IP; Timothy D. Snowden; Yau H. Chan

(57) ABSTRACT

Apparatus and associated methods relate to using a lead ribbon with a catheter. In an illustrative example, the lead ribbon may include exposed electrode pads disposed on a surface in electrical communication with a conductive trace running towards a proximal end of the lead ribbon. For example, the lead ribbon may be bent and inserted within the catheter. For example, a bent end of the lead ribbon may be disposed at the catheter distal end. For example, in a deploy mode, the bent end extends out of the catheter distal end to form a lead ribbon ring. For example, the lead ribbon ring may engage a lumen of tissue and the exposed electrode pads may be oriented radially outward from the horizontal plane in electrical contact with the tissue. Various embodi-
(Continued)

ments may advantageously provide a cost effective. damage mitigated, and size adjustable intro vivo simulation device.

20 Claims, 16 Drawing Sheets

Related U.S. Application Data which is a continuation of application No. 16/858, 452, filed on Apr. 24, 2020, now Pat. No. 11,446,485.

(60) Provisional application No. 62/839,357, filed on Apr. 26, 2019.

(51) Int. Cl.
*A61N 1/05* (2006.01)
*A61N 1/375* (2006.01)

(56) References Cited

U.S. PATENT DOCUMENTS

| | | | | |
|---|---|---|---|---|
| 5,531,778 | A * | 7/1996 | Maschino | A61N 1/0556 607/118 |
| 6,638,237 | B1 | 10/2003 | Guiles et al. | |
| 7,920,928 | B1 * | 4/2011 | Yang | A61N 1/0587 607/130 |
| 7,949,411 | B1 * | 5/2011 | Yang | A61N 1/057 607/122 |
| 8,417,343 | B2 * | 4/2013 | Bolea | A61N 1/3606 607/42 |
| 9,314,633 | B2 * | 4/2016 | Osorio | A61N 1/0551 |
| 9,486,628 | B2 * | 11/2016 | Christopherson | A61N 1/37205 |
| 9,802,038 | B2 * | 10/2017 | Lee | B23K 26/40 |
| 10,207,103 | B2 | 2/2019 | Gonzalez et al. | |
| 10,695,556 | B2 * | 6/2020 | Mercanzini | A61B 5/0536 |
| 10,864,374 | B2 * | 12/2020 | Hoffer | A61N 1/05 |
| 10,980,999 | B2 * | 4/2021 | Wong | A61N 1/048 |
| 2005/0004627 | A1 | 1/2005 | Gibson et al. | |
| 2008/0243217 | A1 * | 10/2008 | Wildon | A61N 1/0587 607/116 |
| 2009/0248122 | A1 * | 10/2009 | Pianca | A61N 1/0551 29/825 |
| 2009/0275996 | A1 | 11/2009 | Burnes et al. | |
| 2009/0275997 | A1 * | 11/2009 | Faltys | A61N 1/36053 607/2 |
| 2012/0197372 | A1 * | 8/2012 | Burgher | A61N 1/0558 607/118 |
| 2013/0245733 | A1 * | 9/2013 | Yomtov | A61N 1/3758 607/116 |
| 2014/0296954 | A1 | 10/2014 | Wells | |
| 2015/0164514 | A1 * | 6/2015 | Wlodarski | A61B 17/164 219/121.72 |
| 2017/0340891 | A1 | 11/2017 | Boggs et al. | |
| 2022/0118261 | A1 * | 4/2022 | Pedersen | A61N 1/056 |

OTHER PUBLICATIONS

Park, et al, Biopsy Needle Integrated with Electrical Impedance Sensing Microelectrode Array towards Real-time Needle Guidance and Tissue Discrimination, Scientific Reports vol. 8, Article No. 264 (2018), retrieved online on Jan. 22, 2020 from https://www.nature.com/articles/s41598-017-18360-4, 37 pages, published on Jan. 10, 2018.

Scheiner, et al, Design and clinical application of a double helix electrode for functional electrical stimulation, IEEE Transactions, retrieved online on Jan. 22, 2020 from https://www.semanticscholar.org/paper/Design-and-clinical-application-of-a-double-helix-Scheiner-Polando/07cd0757c2cc4ffca44dd025000df0dbe0480958, 6 pages, published on 1999.

* cited by examiner

LEAD FOR THE TEMPORARY STIMULATION OF A PERIPHERAL NERVE

CROSS-REFERENCE TO RELATED APPLICATIONS

This application is a continuation-in-part of and claims the benefit of U.S. application Ser. No. 17/816,645, titled "Lead for the temporary stimulation of a peripheral nerve," filed by John Swoyer, et al., on Aug. 1, 2022 and issued Jan. 30, 2024 as U.S. Pat. No. 11,883,651, which is a continuation of and claims the benefit of U.S. application Ser. No. 16/858,452, titled "Lead for the temporary stimulation of a peripheral nerve," filed by John Swoyer, et al., on Apr. 24, 2020 and issued Sep. 20, 2022 as U.S. Pat. No. 11,446,485, which claims the benefit of U.S. Provisional Application Ser. No. 62/839,357, titled "Lead for the temporary stimulation of a peripheral nerve," filed by John Swoyer, et al., on Apr. 26, 2019.

This application incorporates the entire contents of the foregoing application(s) herein by reference.

TECHNICAL FIELD

Various embodiments relate generally to design of a temporary neurostimulation lead.

BACKGROUND

There are a variety of therapies that involve the stimulation of nerves (e.g., peripheral nerves, cardiac tissue) for the treatment of disease states. Some of these therapies may be chronic, and others may be acute. For example, sacral nerve stimulation may be an example of chronic stimulation of a nerve for the treatment of overactive bladder and other disorders of the pelvic area. Stimulation of nerves near a joint or muscle may be used for temporary relief of acute pain, while a chronic implant may be used for long-term pain.

SUMMARY

Apparatus and associated methods relate to a lead that includes metallic traces sandwiched between layers of polymers to form a ribbon (e.g., similar to a flex circuit). In an illustrative example, areas on both ends of the traces may be exposed, forming stimulation electrodes on one end and electrical contacts on the other. The ribbon may be formed such that it fits down a small diameter needle. When the needle is removed, the formed ribbon may relax and engage the tissue providing a means of retention. The lead may advantageously: (1) be minimally invasive to implant, (2) be inexpensive, (3) stay in place in a temporary/trial medical procedure setting, and (4) be easy to remove.

Apparatus and associated methods relate to using a lead ribbon with a catheter. In an illustrative example, the lead ribbon may include exposed electrode pads disposed on a surface in electrical communication with a conductive trace running towards a proximal end of the lead ribbon. For example, the lead ribbon may be bent and inserted within the catheter. For example, a bent end of the lead ribbon may be disposed at the catheter distal end. For example, in a deploy mode, the bent end extends out of the catheter distal end to form a lead ribbon ring. For example, the lead ribbon ring may engage a lumen of tissue and the exposed electrode pads may be oriented radially outward from the horizontal plane in electrical contact with the tissue. Various embodiments may advantageously provide a cost effective. damage mitigated, and size adjustable intro vivo simulation device.

Additional uses include stimulation of cranial nerves, included but not limited to the Vagus nerves to treat conditions, including but not limited to, depression or insomnia. The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Not all patients respond to stimulation treatments. Therefore, in some situations, it may be desirable to have a trial stimulation to demonstrate efficacy prior to an expensive and invasive procedure to implant a chronic system. To be useful, a temporary/trial procedure may use a lead that is minimally invasive to implant, in a setting such as a doctor's office, be inexpensive, stay in place during the trial, and be easy to remove. Accordingly, disclosed herein is a lead designed to meet the above described requirements.

Figure 1:
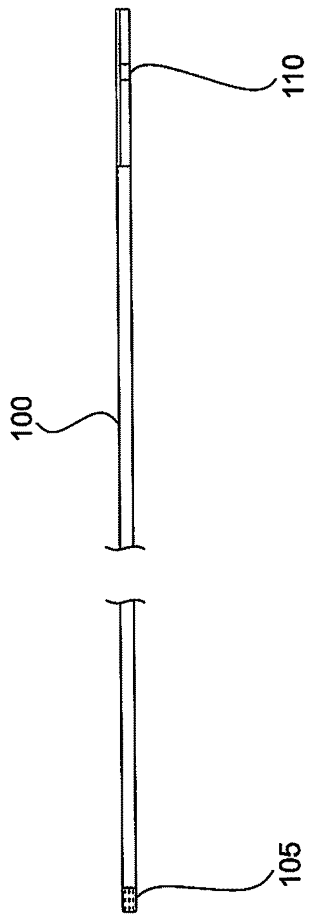
FIGS. 1, 1A, 1, and 1C depict various top perspective views of an exemplary lead ribbon including two traces with exposed ends.
Figure 1A:
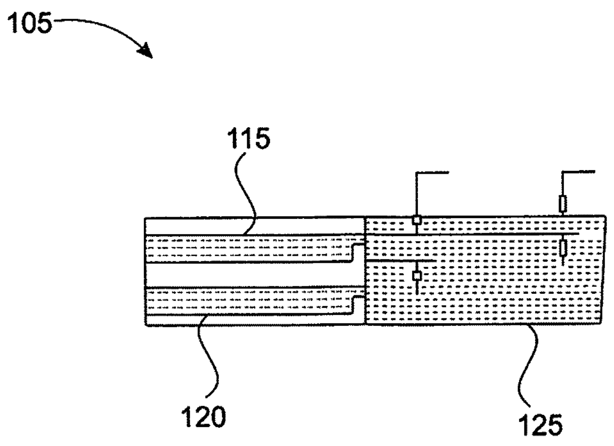
Figure 1B:
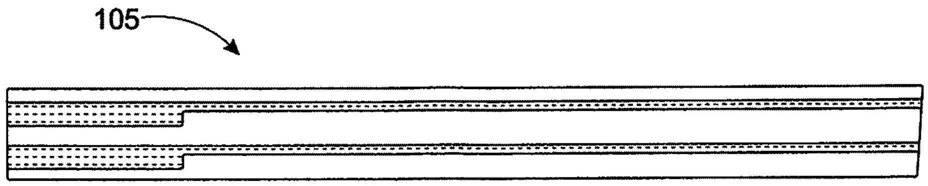
Figure 1C:
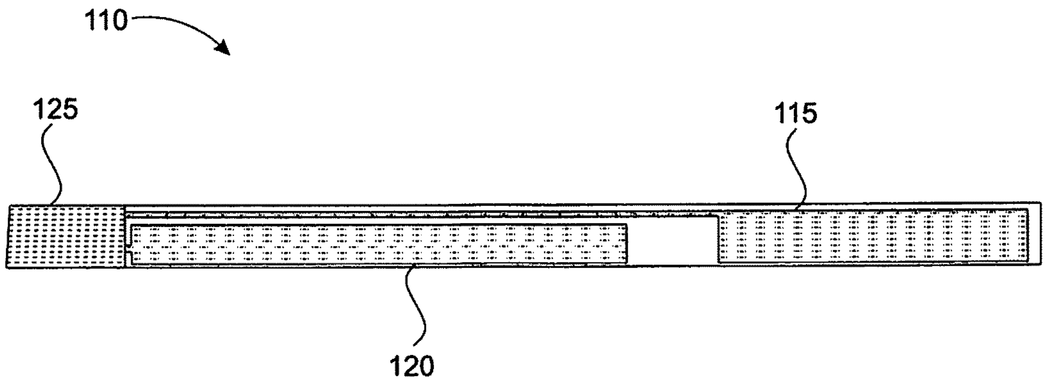

FIGS. 1, 1A, 1, and 1C depict various top perspective views of an exemplary lead ribbon including two traces with exposed ends. These figures show the lead ribbon 100 (with exemplary dimensions) having two traces 115, 120 with exposed ends. FIG. 1A illustrates finer detail of the proximal end 105 of the straight lead ribbon 100 (detail A shown in FIG. 1), while FIG. 1B illustrates the same detail as FIG. 1A but with the top layer of insulation removed to reveal more of the traces.

FIG. 1C illustrates finer detail of the distal end 110 of the lead ribbon 100 (detail B shown in FIG. 1). The traces 115, 120 may be covered with insulation 125 (e.g., polyimide), with one side of each end exposed. The distal end 110 may be configured as electrodes (e.g., a pair of pads), with the proximal exposed end 105 used to connect to an electrical stimulator, or a cable that then connects to a stimulator, for example. It is understood that any number, shape or size of traces, electrodes, and connections could be formed in this manner.

Figure 2:
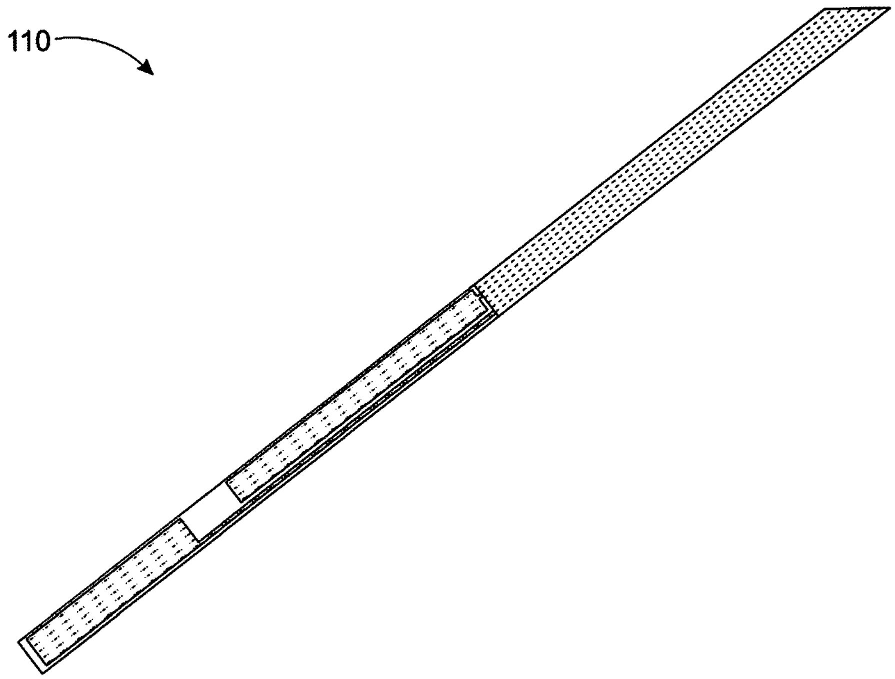
FIG. 2 depicts a perspective view of an exemplary lead, with zoomed in detail on the distal end of the lead illustrating exposed electrodes.

FIG. 2 depicts a perspective view of an exemplary lead, with zoomed in detail on the distal end of the lead illustrating exposed electrodes. This figure shows a close up of the distal end 110, revealing the two exposed electrodes.

Figure 3:
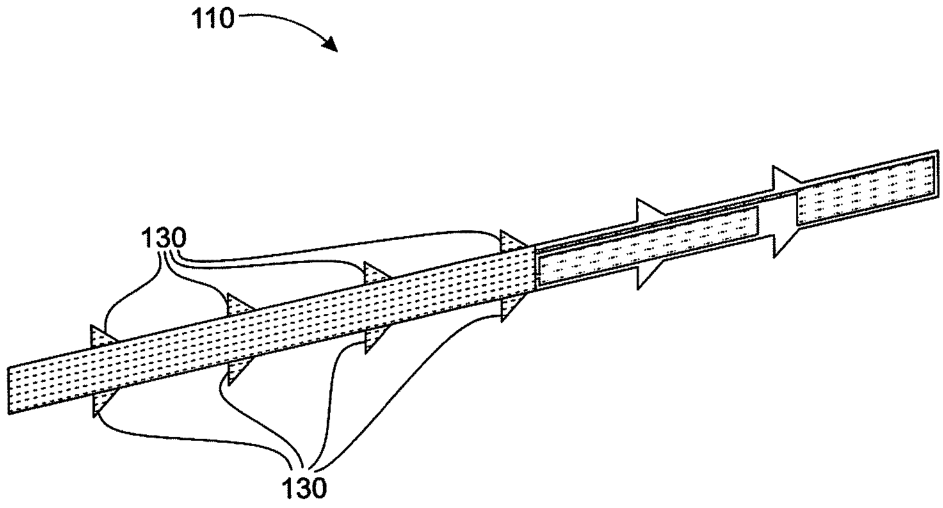
FIG. 3 depicts a perspective view of an exemplary lead, with zoomed in detail on the distal end of the lead illustrating fixation members.

FIG. 3 depicts a perspective view of an exemplary lead, with zoomed in detail on the distal end of the lead illustrating fixation members. In some embodiments, the distal end 110 with optional fixation features/members 130. The fixation members 130 may be formed as multiple teeth, each having a triangular profile, for example. The members 130 may be designed such that they add facilitate additional engagement with surrounding tissue. It is understood that a variety of shapes and sizes could be used, and the features could be located anywhere along the lead ribbon.

Figure 4A:
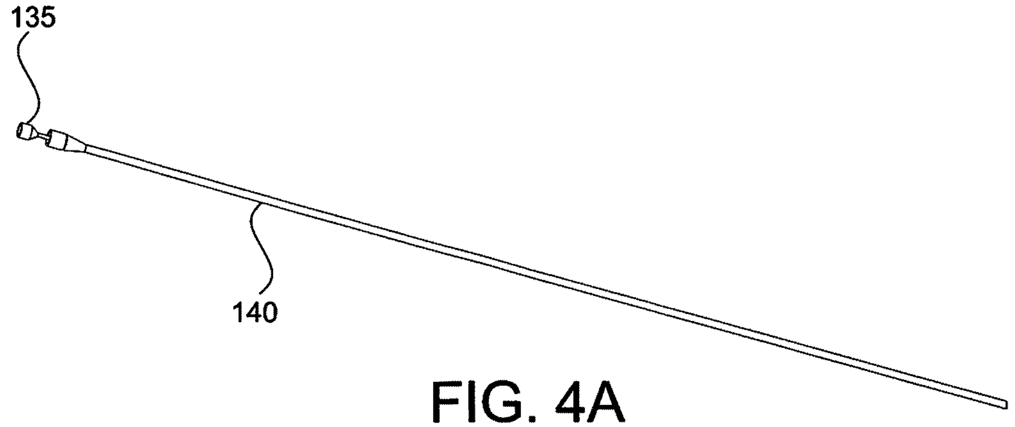
FIGS. 4A, 4B, and 4C depict perspective views of an exemplary lead ribbon installed in a needle with a stylet.
Figure 4B:
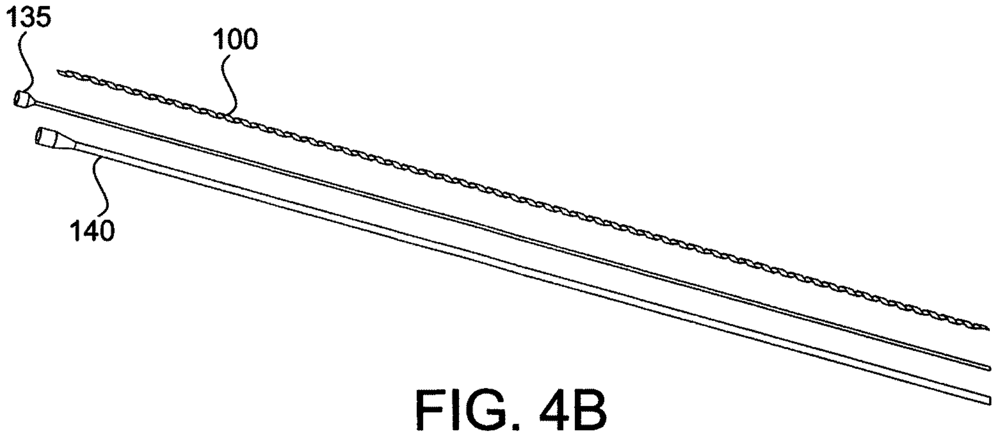
Figure 4C:
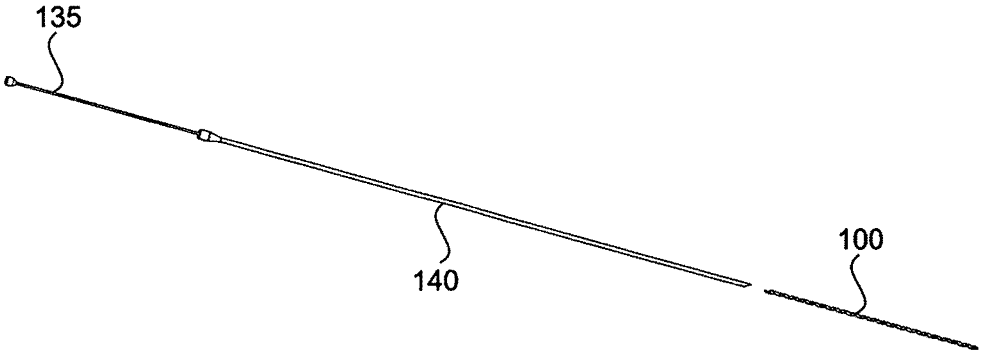

FIGS. 4A, 4B, and 4C depict perspective views of an exemplary lead ribbon installed in a needle with a stylet. A stylet 135 is inserted in a (hollow) needle 140, with a lead ribbon 100 residing inside of the needle 140. The lead ribbon is installed in the needle with the stylet.

Figure 5A:
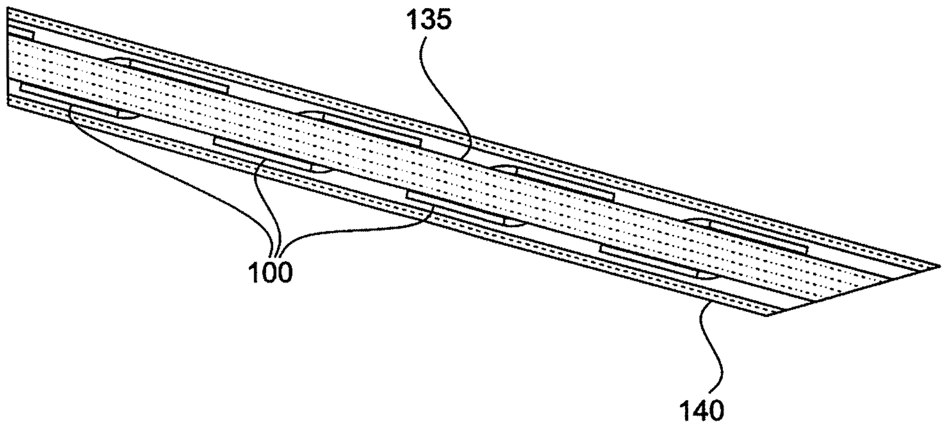
FIGS. 5A and 5B depict cross-sectional views (longitudinal and lateral cross sections) of an exemplary needle, stylet, and lead assembly.
Figure 5B:
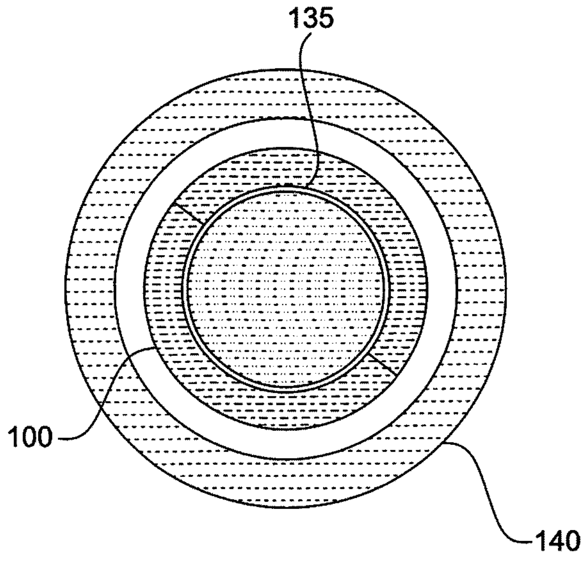

FIGS. 5A and 5B depict cross-sectional views (longitudinal and lateral cross sections) of an exemplary needle, stylet, and lead assembly. The longitudinal and lateral cross section of the assembly reveals the lead ribbon 100 wrapped around the stylet 135 within the needle 140, prepared for insertion into the patient.

Figure 6:
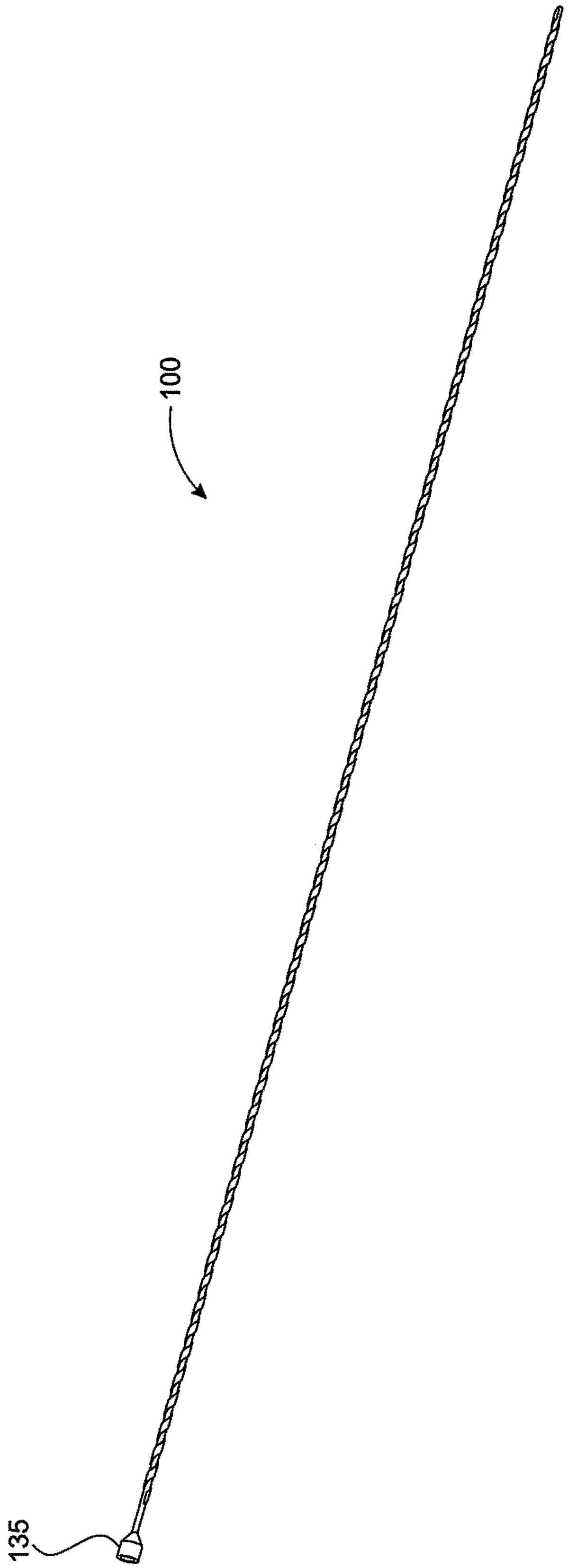
FIG. 6 depicts a perspective view of an exemplary ribbon lead wrapped around an exemplary stylet.

FIG. 6 depicts a perspective view of an exemplary ribbon lead wrapped around an exemplary stylet. After insertion into a patient near the stimulation target, the needle 140 may be withdrawn, as shown in FIG. 6.

Figure 7:
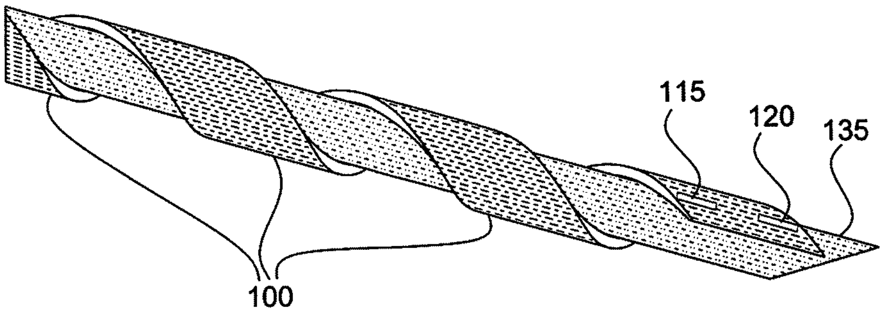
FIG. 7 depicts a perspective view of a distal end of an exemplary lead and stylet assembly.

FIG. 7 depicts a perspective view of a distal end of an exemplary lead and stylet assembly. This illustration shows a detailed view with the needle removed (traces and fixation features are not shown for clarity). In some examples, the stylet may advance to push the lead out of the tip, which may allow the lead to spring open and catch the surrounding tissue. Then the stylet may be slid out, and then the needle slid out over the lead.

Figure 8:
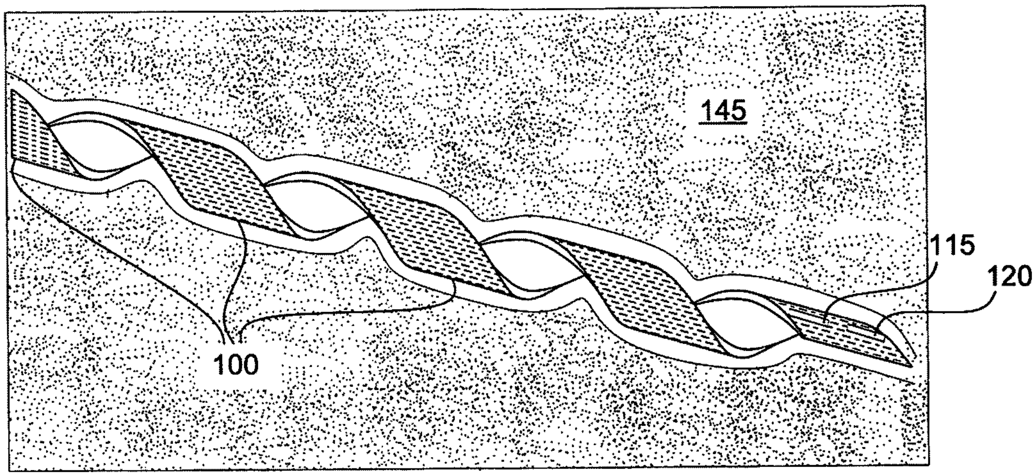
FIG. 8 depicts a perspective view of an exemplary lead embedded inside tissue.

FIG. 8 depicts a perspective view of an exemplary lead embedded inside tissue. Once the needle is removed, and the stylet withdrawn, the spiral wound lead ribbon 100 will tend to expand radially, engaging the tissue as shown in FIG. 8. The (optional) fixation members/features (not shown) may provide additional engagement with the surrounding tissue 145. The spiral form of the ribbon may allow some stretch of the lead as the patient moves, minimizing the chance of dislodgement. When it is time to remove the lead, the proximal end of the ribbon can be grasped and pulled. This may cause the ribbon to unwind and easily come out of the patient.

Figure 9:
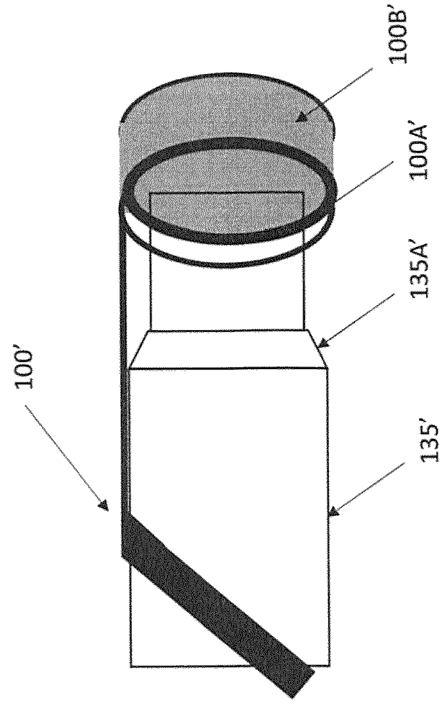
FIG. 9 depicts a side elevation view of an exemplary ribbon wrapped around a stepped stylet to form an inner wrap and an outer wrap.

FIG. 9 depicts a side elevation view of an exemplary ribbon wrapped around a stepped stylet to form an inner wrap and an outer wrap. As seen in FIG. 9, a ribbon 100' is featured that is wrapped more than 360 degrees around a stylet 135'. The stylet 135' includes an area providing a step or shoulder 135A' for the stylet 135' to push against the ribbon 100'. The ribbon 100' is wrapped greater than 360 degrees, such that the ribbon 100' forms an inner ribbon wrap 100A' and an outer ribbon wrap 100B'. The step/shoulder 135A' on the stylet 135' engages a step formed between the inner and outer wraps 100A', 100B', which advantageously aids in pushing the ribbon 100' out of the tube (not shown).

Figure 10A:
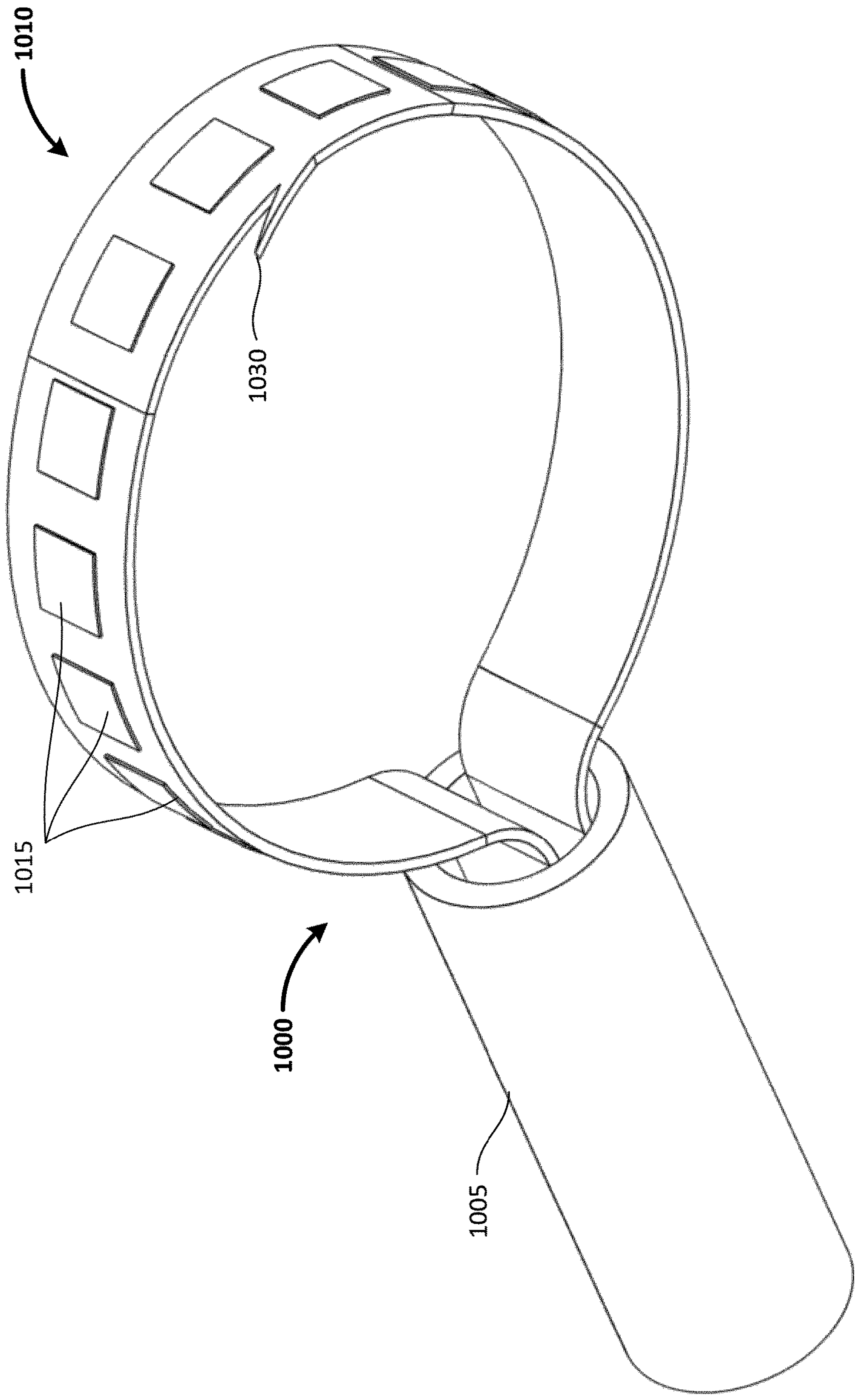
FIG. 10A, FIG. 10B, FIG. 10C, FIG. 10D, FIG. 10E, and FIG. 10F depict perspective views of various embodiments of exemplary ribbon rings introduced by a catheter.

FIG. 10A, FIG. 10B, FIG. 10C, FIG. 10D, FIG. 10E, and FIG. 10F depict perspective views of various embodiments of exemplary ribbon rings introduced by a catheter. As shown in FIG. 10A, a distal end loop 1010 of an exemplary lead ribbon 1000 (e.g., the lead ribbon 100) is introduced by a catheter 1005. In some examples, in an unbent state, the lead ribbon 1000 may be substantially flat. As shown, the distal end loop 1010 may be formed by bending a lead ribbon 1000 (e.g., the lead ribbon 100) in between a distal end and a proximal end of the lead ribbon 1000. In some implementations, the distal end loop 1010 may also be introduced using a needle and a stylet as described with reference to FIGS. 4A-C.

The catheter 1005, for example, may be a 3 French (Fr) catheter. Depending on the application and the size of the exemplary lead ribbon 1000, other sizes of catheter may be used. For example, the catheter 1005 may be a 5 Fr catheter. For example, the catheter 1005 may be a 10 Fr catheter.

In this example, the distal end loop 1010 splits at a distal end (e.g., an opening) of the catheter 1005 to form a loop. For example, the loop shape of the distal end loop 1010 may advantageously prevent damaging surrounding tissues when the distal end loop 1010 is extended out of the catheter 1005.

In some implementations, the lead ribbon 1000 may be made of platinum. In some examples, the lead ribbon 1000 may be made with surgical steel. In some cases, the exemplary lead ribbon 1000 may be made with stainless steel. In some implementations, as a short term implant (e.g., less than 30 days), the lead ribbon 1000 may be made with copper with gold plated to advantageously save costs of manufacturing. For example, the lead ribbon 1000 may be made with nickel with gold plated.

The distal end loop 1010, as shown, includes electrode pads 1015. In some implementations, the electrode pads 1015 may be independently connected to different traces (e.g., the two traces 115). For example, multiple (e.g., groups of 2, 3, 4, 6) electrode pads 1015 may be connected jointly to a single electric trace.

As shown, the distal end loop 1010 includes a fixation member 1030 (e.g., an engagement teeth). For example, the fixation member 1030 may be configured to engage with surrounding tissue to facilitate additional engagement between the distal end loop 1010 and the surrounding tissue. Some embodiments of the fixation member 1030 are described with reference to FIG. 3.

Figure 10B:
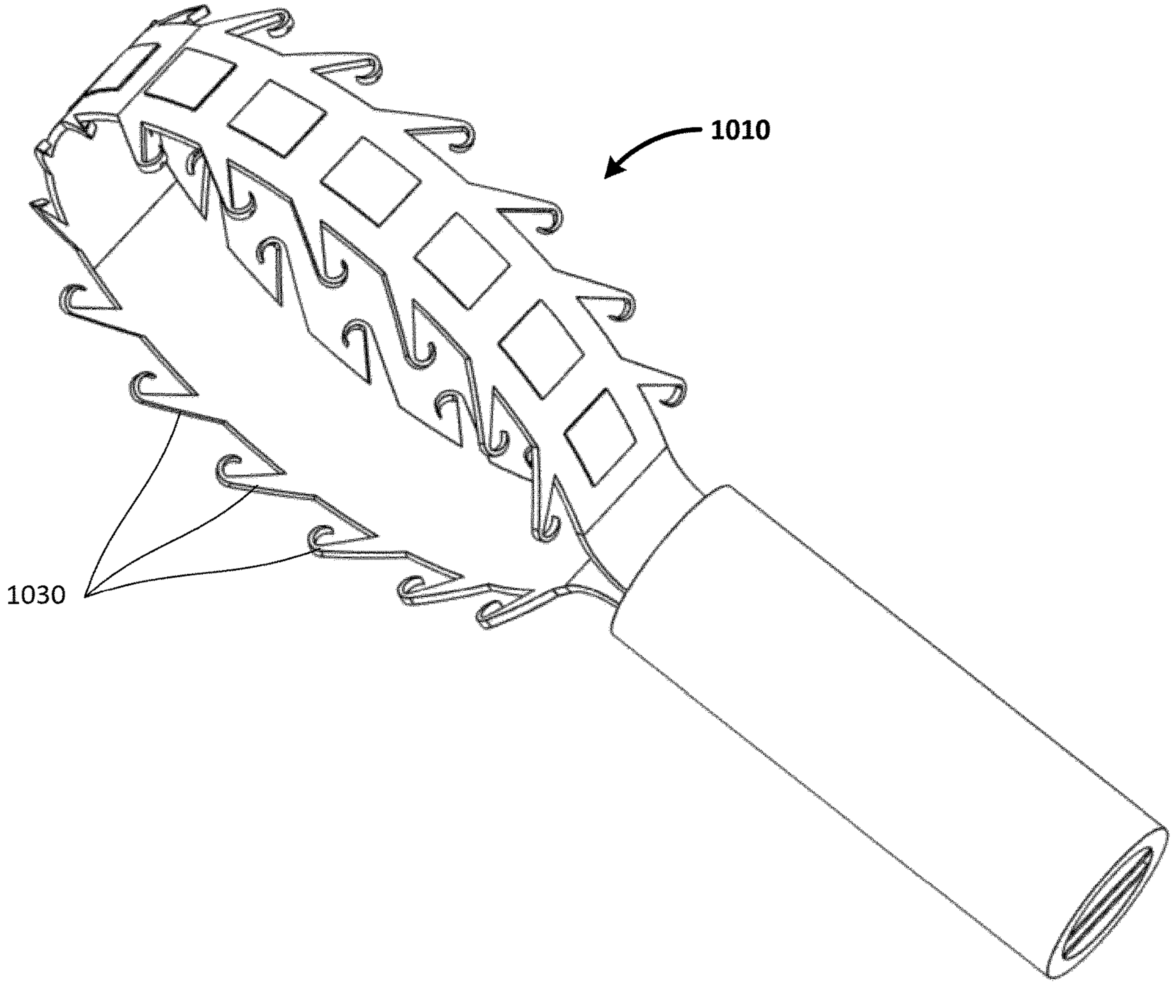
Figure 10C:
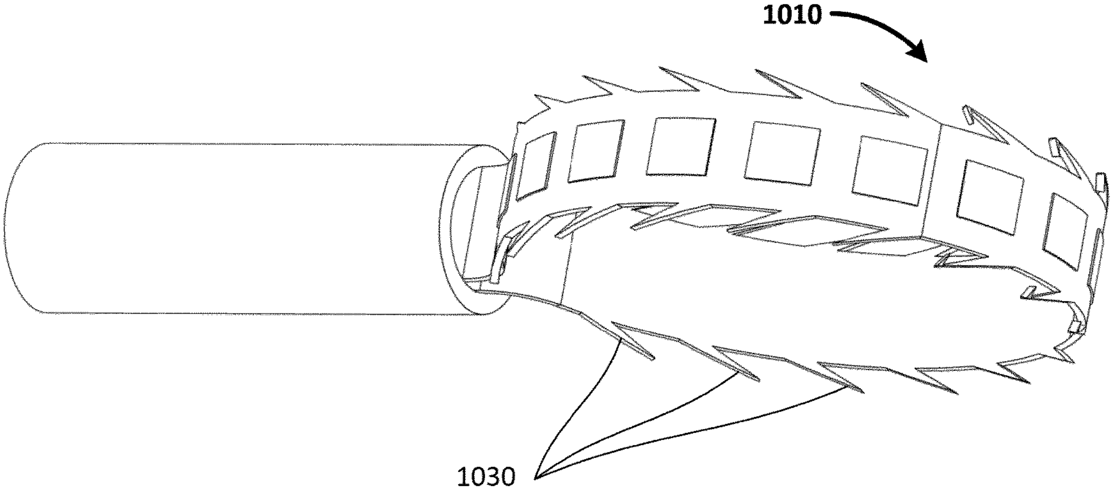
Figure 10E:
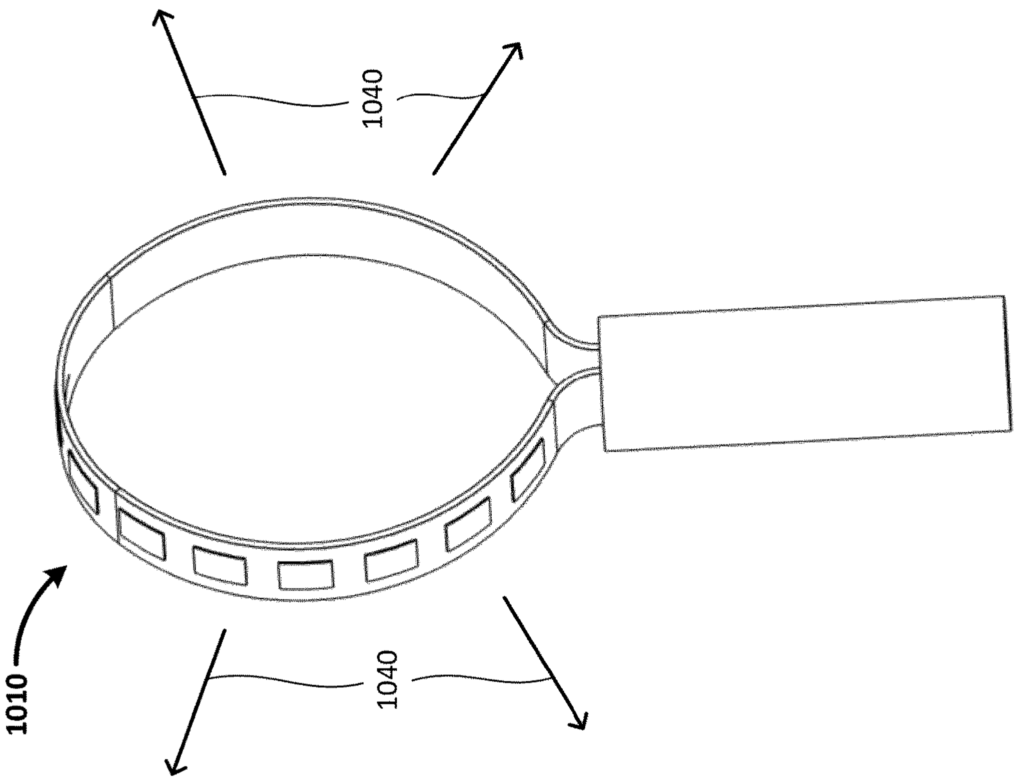
Figure 10D:
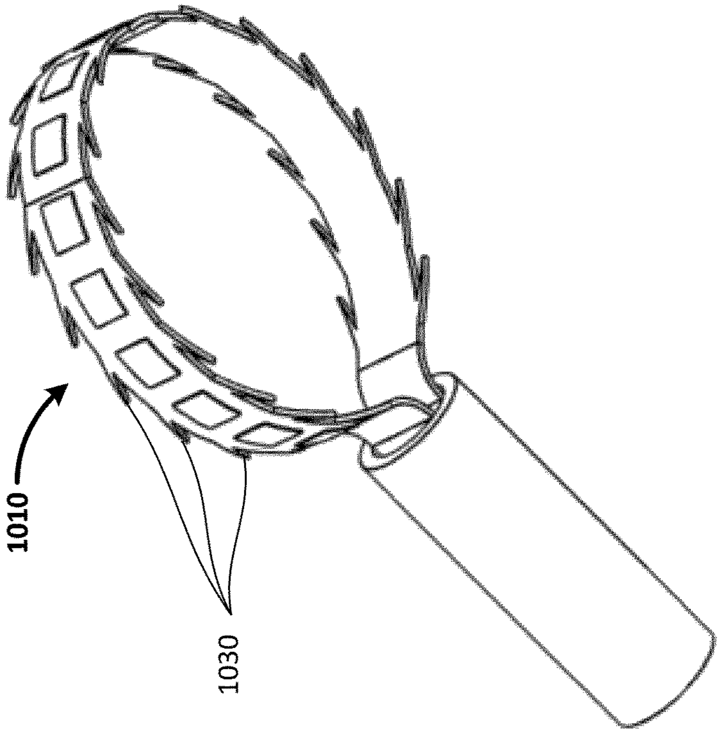

The fixation member 1030 may be in various profiles as shown in FIGS. 10B-D. In some implementations, the fixation member 1030 may be configured to extend in the same direction. For example, when a proximal end of the lead ribbon 1000 is actuated (e.g., pushed or pulled), the fixation member 1030 may disengage with the surrounding tissue to allow the distal end loop 1010 to be retracted. For example, the fixation member 1030 may extend towards a distal end of the lead ribbon 1000. For example, the fixation member 1030 may extend towards the proximal end of the lead ribbon 1000. In some implementations, the fixation member 1030 may include hooks that may be collapsed by retracting the distal end loop 1010 into the catheter 1005.

Figure 10F:
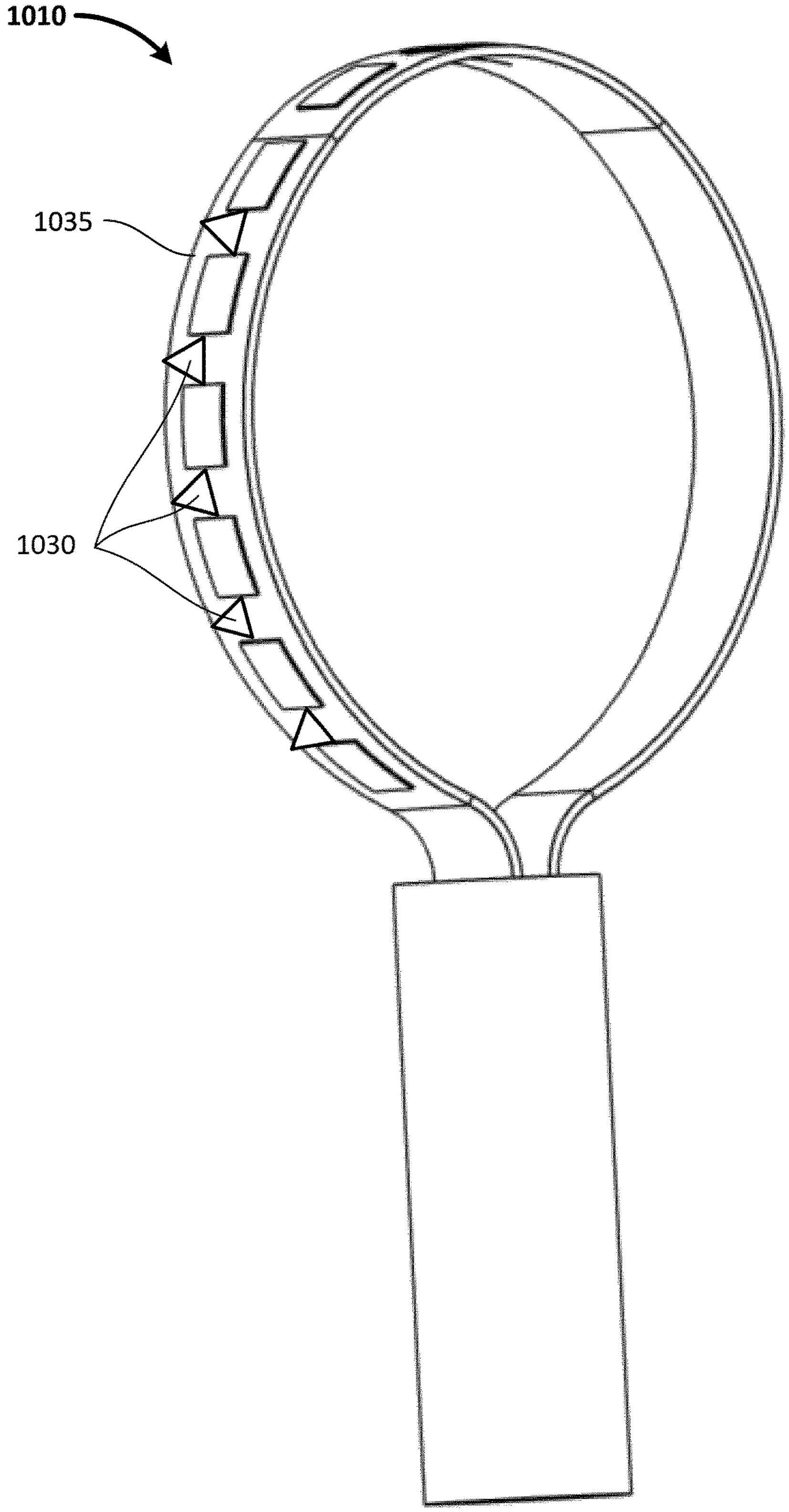

In some implementations, as shown in FIG. 10E, the distal end loop 1010 may be configured without the fixation member 1030. For example, the lead ribbon 1000 may rely on a pressure exerted from the distal end loop 1010 to the surrounding tissue (as shown as arrows 1040) to maintain a position of the distal end loop 1010. In some implementations, the fixation member 1030 may include one or more electrodes (e.g., on its surface). In some implementations, the fixation member 1030 may be extended from a body of the lead ribbon 1000 in multiple planes. For example, the fixation member 1030 may be extended out from a plane 1035 of the electrode pads 1015 as shown in FIG. 10F. For example, the fixation member 1030 may extend perpendicular to an outer surface of the electrode pads 1015. In some implementations, the popping up fixation member shown in FIG. 10F may be cut out from one or more layers of the distal end loop 1010. Various layers of the lead ribbon 1000 are described below with reference to FIGS. 11A-B. In some implementations, the distal end loop 1010 may include a combination of profiles and extension angles/planes as described with reference to FIGS. 10A-F.

Figure 11A:
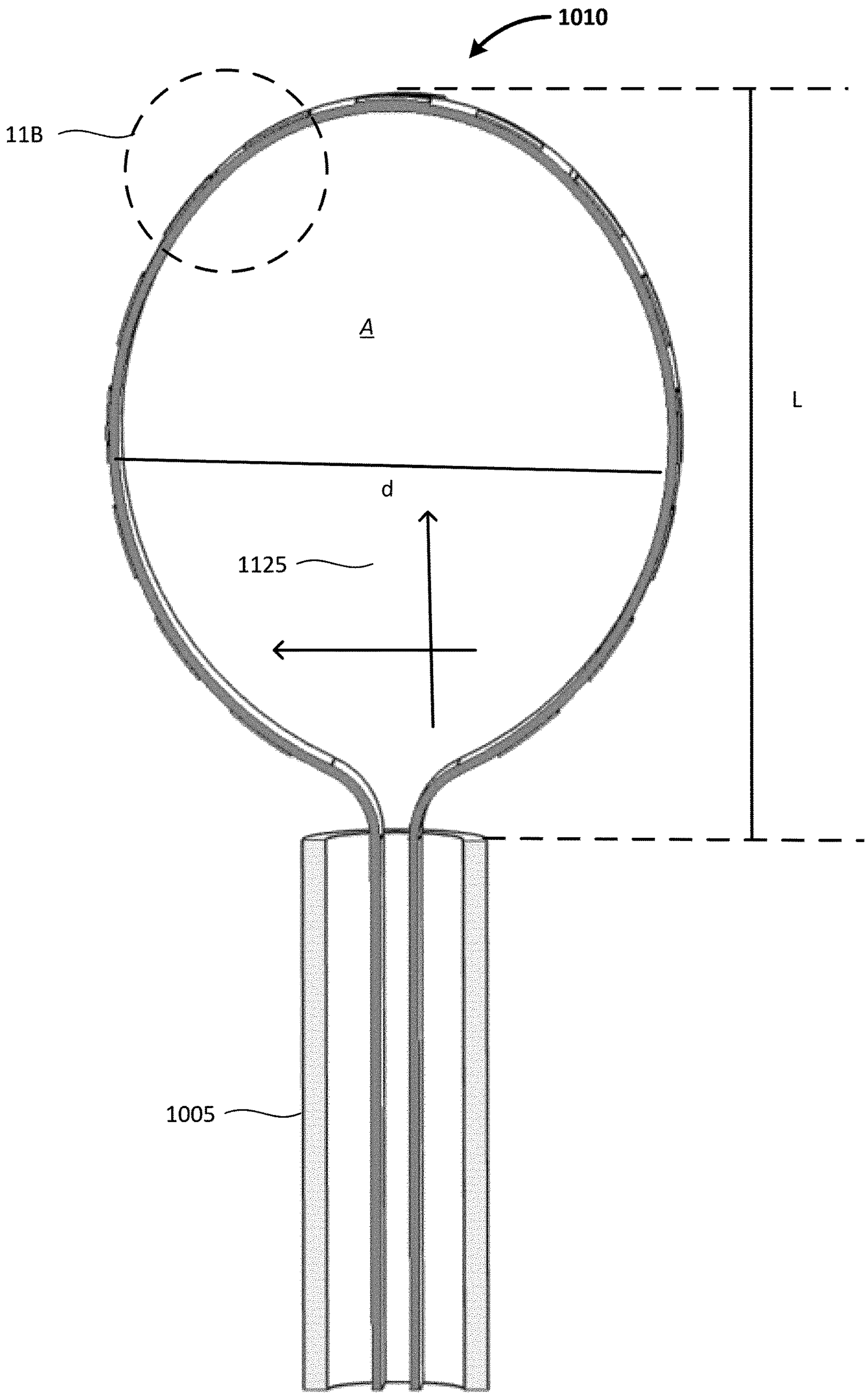
FIG. 11A depicts a cross-section view of an exemplary ribbon lead ring.
Figure 11B:
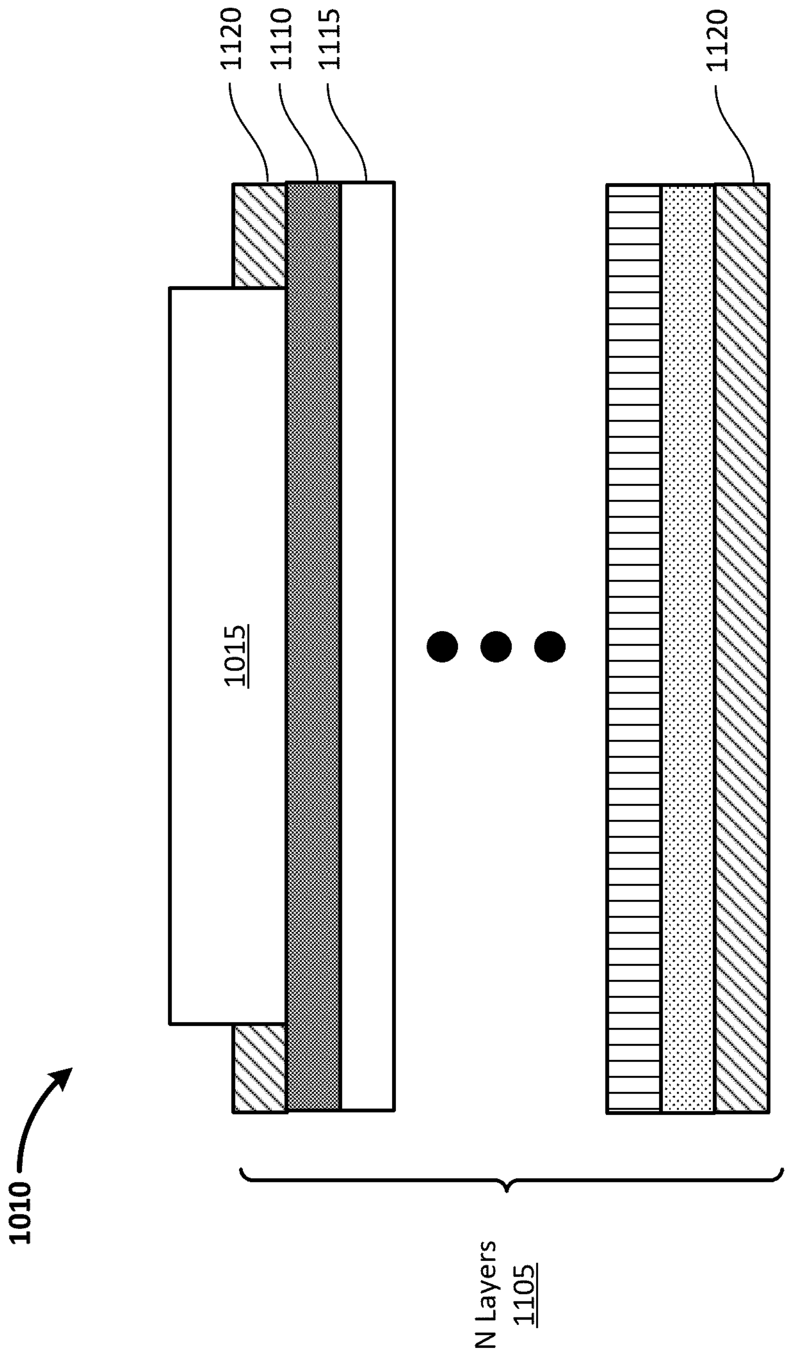
FIG. 11B is a close-up view of a cross-section of FIG. 11A.

FIG. 11A and FIG. 11B depict cross-section views of an exemplary ribbon lead ring. As shown in FIG. 11A, the distal end loop 1010 may split at a proximal end (e.g., as shown at an opening of the catheter 1005) and expand into a ring shape with a diameter of d. For example, the diameter d may be a minimum (or maximum) distance between two points at 180 degree of a plane of the ring. In some implementations, the distal end loop 1010 may include a minimum bending radius. For example, the lead ribbon 1000 may include a minimum bending radius at a predetermined multiples (e.g., 1-2) of a thickness of the lead ribbon 1000.

As shown, when the distal end loop 1010 is formed at the distal end of the catheter 1005 by a bent lead ribbon 1000, a ring of the bent lead ribbon may define a horizontal plane 1125. For example, in a deploy mode, the lead ribbon ring may engage a lumen of tissue. For example, the electrode pads 1015 may be oriented radially outward from the horizontal plane. For example, the electrode pads 1015 may be in electrical contact with the tissue. For example, the fixation member 1030 may be extending in a vertical plane orthogonal to the horizontal plane as shown in FIGS. 10A-C. For example, the fixation member 1030 may be extending in parallel with the horizontal plane as shown in FIG. 10F.

FIG. 11B shows a cross-section view of a close-up diagram of the distal end loop 1010. As shown, the distal end loop 1010 may include multiple (N) layers 1105. For example, a single layer may be 0.001"-0.003". The layers 1105 may include one or more copper trace layers 1110 in this example. In some other examples, other conductive layer(s) may be used. For example, the one or more copper trace layers 1110 may be 0.001" thick. For example, the copper trace layer 1110 may be operably coupled to the electrode pads 1015. In some implementations, the one or more copper trace layers 1110 may include 18 traces.

For example, the layers 1105 may also include a base layer 1115. For example, the base layer 1115 may be polyamide. For example, the base layer 1115 may include PET (Polyethylene terephthalate). In some examples, the PET base layer may advantageously be pliable.

In some implementations, the layers 1105 may include a control layer. For example, the control layer may include a control wire for retracting and extending the distal end loop 1010 at the end of the catheter.

In this example, the one or more copper trace layers 1110 and the base layer 1115 are covered by a coating layer 1120. In various implementations, there may be more layers in between the coating layer 1120 and the one or more copper trace layers 1110. In various implementations, there may be more layers in between the coating layer 1120 and the base layer 1115. In some implementations, the ordering of the one or more copper trace layers 1110, the coating layer 1120, and/or the base layer 1115 may be reordered in all combinations possible.

In some implementations, the coating layer 1120 may be a soft and flexible material. For example, the coating layer 1120 may include silicone molded over the top of other layers of the layers 1105. For example, the distal end loop 1010 may be round and soft with the silicone outer layer. For example, the soft and flexible silicone outer layer may prevent a distal end of the distal end loop 1010 from damaging the surrounding tissue.

In some implementations, the fixation member 1030 may also include multiple layers. For example, the multiple layered fixation member may include a silicone (flexible) teeth. For example, the fixation member 1030 with a flexible teeth may be softer on an outer layer to advantageously prevent the fixation member 1030 from accidentally damaging the surrounding tissue.

In various implementations, the layers 1105 of the distal end loop 1010 may be premanufactured. Then the lead ribbon 1000 may be produced by molding/cutting/stamping into desired length. In some implementations, two or more lead ribbon 1000 may be soldered to each other.

Figure 12:
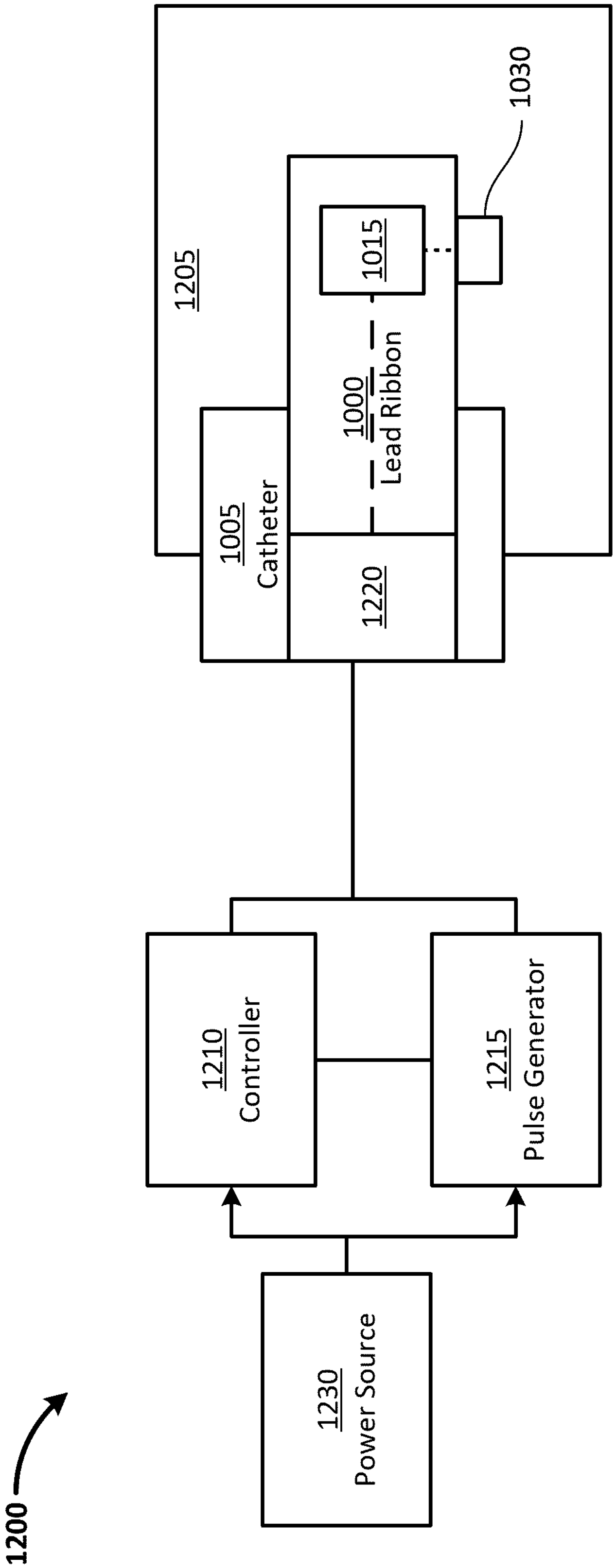
FIG. 12 is a block diagram showing an exemplary temporary pacing system.

FIG. 12 is a block diagram showing an exemplary temporary pacing system (TPS 1200) using a lead ribbon. In this example, the lead ribbon 1000 is introduced to a surrounding tissue 1205 using the catheter 1005. The lead ribbon 1000, in this example, is coupled to a controller 1210 and a pulse generator 1215. In this example, the lead ribbon 1000 may be delivered to a surrounding tissue 1205 (e.g., at an apex of a heart) by the catheter 1005.

In some implementations, the lead ribbon 1000 may be controlled by a manifold coupled to the proximal end of the lead ribbon 1000. In this example, the lead ribbon 1000 includes a header 1220. For example, the header 1220 may be coupled to the pulse generator 1215. For example, the pulse generator 1215 may supply electric pulse(s) to the electrode pads 1015. In some implementations, the lead ribbon 1000 may be connected to the pulse generator 1215 using medical alligator clips. For example, the controller 1210 and/or the pulse generator 1215 may be powered by a power source 1230 (e.g., a battery, a wall plug, a DC power supply).

In this example, the lead ribbon lead ribbon lead ribbon 1000 is also coupled to the controller 1210. For example, the controller 1210 may control one or more nitinol wires embedded in one or more of the layers 1105 within the lead ribbon 1000. For example, by controlling the nitinol wires, the controller 1210 may manipulate the lead ribbon 1000 to be deployed at a desired location within the surrounding tissue 1205. In some implementations, the controller 1210 may include a switch. For example, the switch may be configured to allow a user to manually control the distal end loop 1010 of the lead ribbon 1000. For example, a user may use the controller 1210 to extend and/or retract the distal end loop 1010 out of the catheter 1005. For example, an extension L may change the diameter d as discussed with reference to FIG. 11A. For example, when the extension L increases, an area A defined by the distal end loop 1010 may increase (e.g., directly related, directly proportional to, monotonically related). In some implementations, the controller 1210 may include a motorized mechanism to automatically (e.g., assistively) operate the lead ribbon 1000 within the surrounding tissue 1205.

In some implementations, the lead ribbon 1000 in the TPS 1200 may be replaced by the lead ribbon 100 as described with reference to FIGS. 1-8.

In various implementations, some or all of the controller 1210, the pulse generator 1215, and the power source 1230 may be embedded in one or more unitary housing. For example, the power source 1230, the controller 1210 and/or the pulse generator 1215 may be embedded in a handle. For example, a user (e.g., a surgeon) may use the handle to operate the lead ribbon 1000 in the surrounding tissue 1205.

In some implementations, the electrode pads 1015 may be used as sensors or other actuators. For example, the electrode pads 1015 may be used to supply power and provide communication channels (e.g., to transmit command signals and receive sensor data). For example, the electrode pads 1015 may be connected to a vision sensor. For example, the electrode pads 1015 may be coupled to a temperature sensor.

In some implementations, the catheter 1005 may include communication layers having traces for transmitting and/or receiving communication signals from the fixation member 1030 or the electrode pads 1015. For example, the fixation member 1030 may include a sensor configured to measure health data (e.g., temperature, pressure, pH value) of the surrounding tissue 1205. Through the communication layers, the controller 1210 may receive the sensor data.

Figure 13:
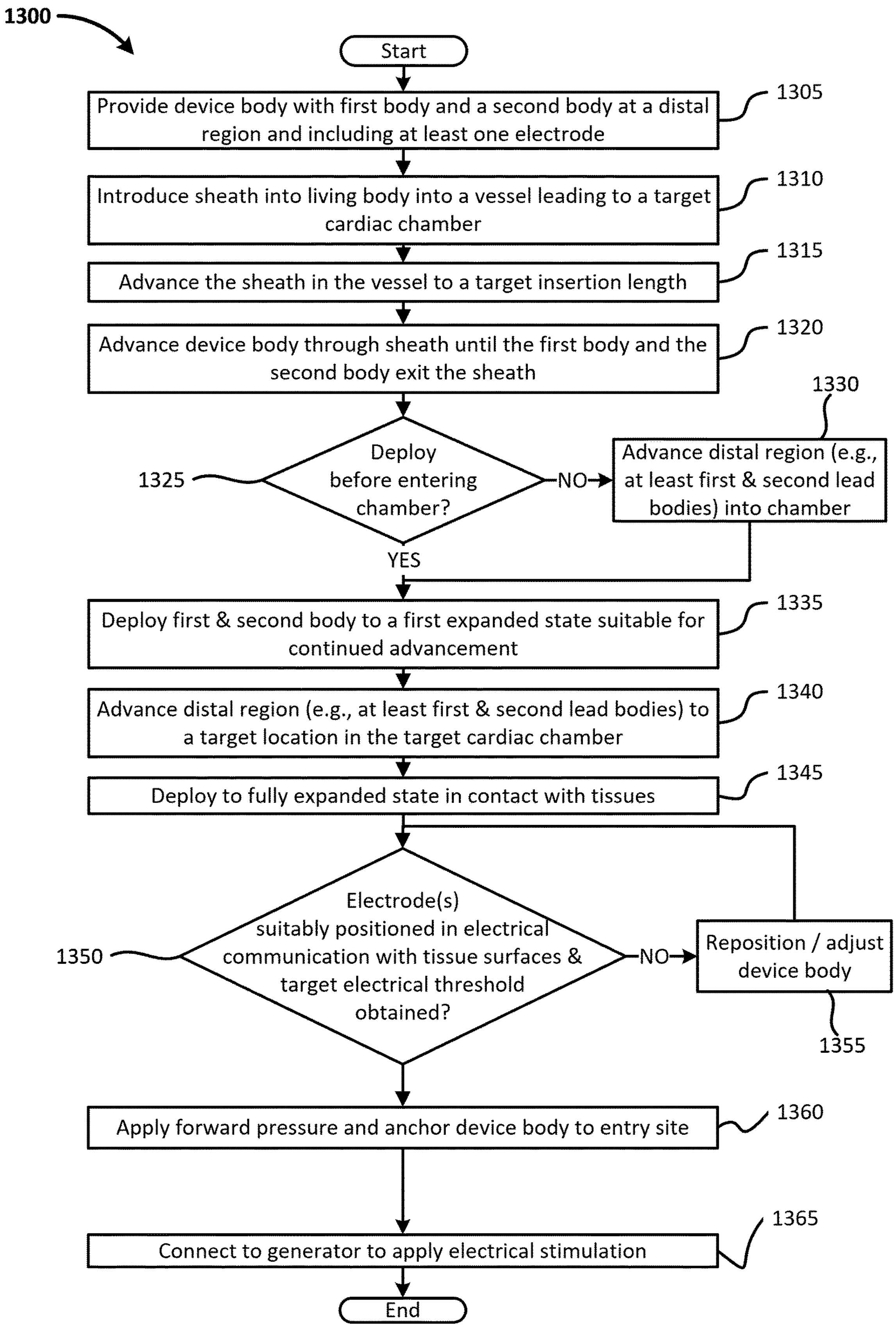
FIG. 13 depicts an illustrative method of temporary stimulation using, for example, any of the embodiments disclosed at least with reference to FIGS. 1-12.

FIG. 13 depicts an illustrative method 1300 of temporary stimulation using, for example, any of the embodiments disclosed at least with reference to FIGS. 1-12. In a step 1305, a device body is provided. The device body (e.g., the lead ribbon 1000) may, for example, include at least one electrode coupled to an electrode conduction wire (e.g., conducting trace in the one or more copper trace layers 1110) extended through a proximal end of the device body.

A sheath is introduced, at a step 1310 into a living body (e.g., at a groin entry point, at a neck entry point). The sheath (e.g., the catheter 1005) may be introduced into a vessel leading to a target cardiac chamber (e.g., the right ventricle). In a step 1315, the sheath is advanced in the vessel to a target insertion length. The device body is advanced, in a step 1320, through the sheath until the expanding distal end (e.g., the distal end loop 1010) exits the sheath.

If it is determined, in a decision point 1325, not to at least partially deploy the expanding distal end before entering the target chamber, then the distal region (e.g., the distal end loop 1010) is advanced into the target cardiac chamber in a step 1330.

If it is determined, in the decision point 1325, to at least partially deploy prior to entering the target chamber (e.g., to operate into a partially expanded state, such as to reduce a risk of puncture of tissue), or after step 1330 is completed, then the expanding distal end (e.g., by operating the distal end loop 1010 using the controller 1210) are deployed to a first expanded state (e.g., partially expanded) suitable for continued advancement (e.g., partially expanded without applying excessive pressure to a vessel wall and/or valve aperture) in a step 1335. The distal region is then advanced to a target location (e.g., an apex of the right ventricle) in the target cardiac chamber in a step 1340.

In a step 1345, the expanding distal end (e.g., the first body and the second body) are expanded to a second expanded state (e.g., fully expanded) such that the first body and the second body contact different tissue surfaces (e.g., septum, ventricle wall, opposing myocardial surfaces) within the target cardiac chamber.

In a decision point 1350, it is determined if the electrode (s) are suitably positioned in electrical communication with the tissue surfaces. For example, a surgeon may determine whether the electrode pads 1015 are positioned in the desirable position on a surface of the surrounding tissue 1205. For example, as depicted, suitable positioning may be determined by whether a target electrical threshold is obtained. In some implementations, for example, suitable positioning may be at least partially determined by imaging (e.g., radiography, ultrasound). In some implementations, multiple conductors (e.g., conductor pair combinations) may be tested (e.g., manually, automatically such as by an automatic switch box) to determine if any electrodes are in suitable contact.

If it is determined in the decision point 1350 that the at least one electrode is not suitably positioned, then the device body is repositioned and/or adjusted (e.g., expanded, contracted, rotated, re-shaped such as by differentially expanding/contracting the first and second lead bodies) in a step 1355, and then the method returns to the decision point 1350.

In the method 1300, the device body is anchored (e.g., 'passively fixated') in a desired position (e.g., after decision point 1350 as shown, before decision point 1350 such as after step 1345) by applying forward pressure to the device body in step 1360. In some embodiments, forward pressure may be maintained, such in the example disclosed in FIG. 10A-11B, by anchoring (e.g., suturing) the device body to the entry site of the living body. The device body may, for example, advantageously be anchored thereby in the target cardiac chamber by the forward pressure. In some examples, a Tuohy Borst device may be positioned near the introducer manifold may. The Tuohy Borst device may, for example, be used to frictionally hold the proximal lead body to the introducer and/or maintain the forward pressure of the device body into the cardiac chamber. In step 1365, the electrode(s) are electrically connected to a pulse generator, such as to apply electrical stimulation (e.g., temporary pacing).

Although various embodiments have been described with reference to the Figures, other embodiments are possible. In some implementations, the trace layer may include other electrically conductive materials. For example, the trace layer may include conductive fabrics. For example, the trace layer may include conductive adhesives. For example, the trace layer may include conductive inks. For example, the trace layer may include conductive epoxy.

Although various embodiments are disclosed with reference to temporary cardiac pacing, other implementations are possible. In some examples, the lead body may be used in any cavity in the body.

For example, in some embodiments, a lead body (e.g., the lead ribbon 1000) may be configured and/or used in neurostimulation.

For example, the lead ribbon 1000 may be used for stimulating stomach and/or gastrointestinal (GI) regions.

In some implementations, the lead ribbon 1000 may be used in urology. For example, the distal region 105 may be configured to expand in the bladder, urethra, and/or ureter. For example, the lead ribbon 1000 may be used to prevent spasming, such as after stone removal.

In some implementations, the lead body (e.g., of the lead ribbon 100, the lead ribbon 1000) may be implemented as a deployment platform. For example, the lead ribbon 1000 may be configured as a selectively deployable temporary deployment platform. The lead ribbon 1000 may be provided with one or more sensors (e.g., temperature sensors, pH sensors, camera) and/or actuators (e.g., thermal application devices, electrical application devices). For example, the expanding lead body may serve as a temporary, non-occlusive anchor. For example, the expanding lead body and/or fixation anchor (e.g., as an electrode, as a non-electrode) may be implemented as a temporarily anchored delivery and/or monitoring platform.

In some implementations, for example, a physician may operate the lead body into a desired region, and deploy the lead body. The lead ribbon 1000 may be anchored in place, for example, by shape and/or by deployment of one or more fixation anchors (e.g., the fixation member 1030). In some implementations, for example, one or more effectors (e.g., biopsy tool, surgery tool) and/or sensors (e.g., cameras, analyte detectors, force sensors) may be operated from the platform. In some implementations, one or more effectors may be used for ablation therapy in one or more regions of the body.

In various examples, a lead for temporary stimulation of a peripheral nerve includes a lead ribbon. The lead ribbon may include a lead ribbon substrate. The lead ribbon may include at least one trace running along a length of the lead ribbon substrate between a lead ribbon proximal end to a lead ribbon distal end. The lead ribbon may include a pair of electrodes located at the lead ribbon distal end and in electrical communication with the at least one trace, respectively. The lead ribbon may include at least one exposed electrical stimulation pad located at the lead ribbon proximal end and in electrical communication with the at least one trace. The lead for temporary stimulation of a peripheral nerve may include a stylet. The lead ribbon may be wrapped around the stylet such that an exposed surface of the at least one electrical stimulation pad is oriented radially outward relative to the stylet.

The lead for temporary stimulation of a peripheral nerve may include a hollow needle in which the lead ribbon wrapped around the stylet resides. The at least one trace may be enclosed by electrical insulation, the electrical insulation extending between the lead ribbon proximal end to the lead ribbon distal end. The lead ribbon may be helically wrapped around the stylet. The lead ribbon may include multiple fixation features disposed along the length of the lead ribbon and configured to fixingly engage with surrounding patient tissue. The multiple fixation features include a plurality of teeth located on opposing lateral sides of the lead ribbon. The lead ribbon may include a springing lead ribbon configured to spring open and catch surrounding patient tissue after the lead ribbon is released from the stylet inside a patient. After the lead ribbon is released from the stylet inside the patient, the lead ribbon may be configured to expand radially to retainingly engaging surrounding patient tissue. The lead ribbon may be stretchable along a longitudinal axis defined by the stylet. In some embodiments, the at least one trace may include a pair of traces, the at least one electrode trace may include a pair of electrode, and the at least one exposed electrical stimulation pad trace may include a pair of exposed electrical stimulation pads, the pair of electrodes may be in electrical communication with the pair of traces, respectively, and the pair of exposed electrical stimulation pads may be in electrical communication with the pair of traces, respectively. In some embodiments, the stylet may include a stepped stylet. In some embodiments, the lead ribbon may be configured to wrap around the stylet more than 360 degrees to form an inner ribbon wrap and an outer ribbon wrap.

A method for the insertion of a lead for temporary stimulation of a peripheral nerve may include inserting into an electrical stimulation assembly into a patient proximate to a stimulation target. The electrical stimulation assembly may include a lead ribbon. The lead ribbon may include a lead ribbon substrate, at least one trace running along a length of the lead ribbon substrate between a lead ribbon proximal end to a lead ribbon distal end, at least one electrode disposed at the lead ribbon distal end and in electrical communication with the at least one trace, respectively, and at least one exposed electrical stimulation pads disposed at the lead ribbon proximal end and in electrical communication with the at least one trace, respectively. The electrical stimulation assembly may include a stylet, where the lead ribbon may be helically wrapped around the stylet such that an exposed surface of the at least one electrical stimulation pad is oriented radially outward relative to the stylet. The electrical stimulation assembly may include a hollow needle in which the lead ribbon wrapped around the stylet resides. The method may include advancing the stylet to push the stylet out of a tip of the hollow needle to effectuate springing open of the lead ribbon to catch surrounding tissue. The method may include sliding the stylet out from the surrounding tissue and separating the stylet from the lead ribbon and hollow needle. The method may include sliding the hollow needle out from the surrounding tissue and separating the hollow needle from the lead ribbon. The method may include expanding the helically oriented lead ribbon radially outward to engage the surrounding tissue.

In some embodiments, the at least one trace may include a pair of traces, the at least one electrode may include a pair of electrodes, and the at least one exposed electrical stimulation pad may include a pair of exposed electrical stimulation pads, the pair of electrodes may be in electrical communication with the pair of traces, respectively, and the pair of exposed electrical stimulation pads may be in electrical communication with the pair of traces, respectively. In various implementations, the proximal pads may not be exposed, with connection made via an insulation displacement connector. In such an implementation there would not even need to be a specific pad (per se), and connection could be made to the trace. In such implementations, the lead could be cut off to be made shorter, if so desired.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A system for temporary stimulation of a body tissue, the system comprising:

a lead ribbon substrate comprises:

a substantially flat lead ribbon substrate extending substantially in a first plane when in an unbent state;

at least one trace running along a length of the lead ribbon substrate between a lead ribbon proximal end to a lead ribbon distal end; and at least one exposed electrode pad disposed at the lead ribbon substrate and in electrical communication with the at least one trace;

a catheter comprising a catheter distal end and a catheter proximal end, wherein the lead ribbon substrate is bent between the lead ribbon proximal end and the lead ribbon distal end and inserted within the catheter, wherein a bent end of the lead ribbon substrate is disposed at the catheter distal end; and, a pulse generator operably coupled to the at least one exposed electrode pad through the at least one trace and is configured to generate an electric pulse, wherein, when a switch coupled to the lead ribbon substrate is operated, a position of the bent end relative to an opening of the catheter distal end is configured to move at least in a longitudinal axis out of the catheter distal end, such that a lead ribbon ring is formed at the catheter distal end by the bent end, wherein the lead ribbon ring defines a horizontal plane, such that the lead ribbon ring is configured to engage a lumen of tissue and the at least one exposed electrode pad is oriented radially outward from the horizontal plane and is in electrical contact with the tissue.

2. The system of claim 1, wherein the switch is configured to be controlled manually.

3. The system of claim 1, wherein the lead ribbon substrate further comprises a plurality of fixation features extending in a vertical plane orthogonal to the horizontal plane from at least a first edge of the lead ribbon substrate.

4. The system of claim 3, wherein the lead ribbon substrate comprises a plurality of layers comprising a base layer, an outer layer, and a conductive trace layer, wherein the plurality of fixation features comprises one of the plurality of layers extending in the vertical plane.

5. The system of claim 3, wherein the plurality of fixation features each further comprises an electrode.

6. The system of claim 1, wherein the lead ribbon substrate further comprises a plurality of fixation features extending in the horizontal plane perpendicular to an exposed surface of the at least one exposed electrode pad.

7. The system of claim 1, wherein an area enclosed within the lead ribbon ring is directly proportional to an extension distance of the lead ribbon ring along in the longitudinal axis from the opening of the catheter distal end.

8. The system of claim 1, wherein the lead ribbon substrate comprises an outer layer, wherein the outer layer comprises soft and flexible silicone, such that a distal end of the lead ribbon ring is round and soft such that damage to the tissue is prevented.

9. A system for temporary stimulation of a body tissue, the system comprising:

a lead ribbon substrate comprises:

a substantially flat lead ribbon substrate extending substantially in a first plane when in an unbent state;

at least one trace running along a length of the lead ribbon substrate between a lead ribbon proximal end to a lead ribbon distal end; and at least one exposed electrode pad disposed at the lead ribbon substrate and in electrical communication with the at least one trace; and, a catheter comprising a catheter distal end and a catheter proximal end, wherein the lead ribbon substrate is bent between the lead ribbon proximal end and the lead ribbon distal end and inserted within the catheter, wherein a bent end of the lead ribbon substrate is disposed at the catheter distal end, wherein, in a deploy mode, the bent end extends out of the catheter distal end in a longitudinal axis, such that a lead ribbon ring is formed at the catheter distal end by the bent end, wherein the lead ribbon ring defines a horizontal plane, such that the lead ribbon ring is configured to engage a lumen of tissue and the at least one exposed electrode pad is oriented radially outward from the horizontal plane and is in electrical contact with the tissue.

10. The system of claim 9, further comprises a pulse generator operably coupled to the at least one exposed electrode pad through the at least one trace.

11. The system of claim 9, further comprises a switch operably coupled to a proximal end of the lead ribbon ring, wherein operating the switch controls a position of the lead ribbon ring relative to an opening of the catheter distal end.

12. The system of claim 11, wherein the switch is configured to be controlled manually.

13. The system of claim 9, wherein the lead ribbon substrate further comprises a plurality of fixation features extending in a vertical plane orthogonal to the horizontal plane from at least a first edge of the lead ribbon substrate.

14. The system of claim 13, wherein the lead ribbon substrate comprises a plurality of layers comprising a base layer, an outer layer, and a conductive trace layer, wherein the plurality of fixation features comprises one of the plurality of layers extending in the vertical plane.

15. The system of claim 14, wherein the plurality of fixation features each further comprises an electrode.

16. The system of claim 9, wherein the lead ribbon substrate further comprises a plurality of fixation features extending in the horizontal plane perpendicular to an exposed surface of the at least one exposed electrode pad.

17. The system of claim 9, wherein an area enclosed within the lead ribbon ring is directly proportional to an extension distance of the lead ribbon ring along the longitudinal axis from an opening of the catheter distal end.

18. The system of claim 9, wherein the lead ribbon substrate comprises an outer layer, wherein the outer layer comprises soft and flexible silicone, such that a distal end of the lead ribbon ring is round and soft such that damage to the tissue is prevented.

19. A method for insertion of a lead for temporary stimulation of a peripheral nerve, the method comprising:

inserting an electrical stimulation assembly into a patient proximate to a stimulation target, wherein the electrical stimulation assembly comprises:

a lead ribbon substrate comprising:

a substantially flat lead ribbon substrate extending substantially in a first plane when in an unbent state;

at least one trace running along a length of the lead ribbon substrate between a lead ribbon proximal end to a lead ribbon distal end; and at least one exposed electrode pad disposed at the lead ribbon substrate and in electrical communication with the at least one trace; and, a catheter comprising a catheter distal end and a catheter proximal end, wherein the lead ribbon substrate is bent between the lead ribbon proximal end and the lead ribbon distal end and inserted within the catheter, wherein a bent end of the lead ribbon substrate is disposed at the catheter distal end, wherein, in a deploy mode, the bent end extends out of the catheter distal end in a longitudinal axis, such that a lead ribbon ring is formed at the catheter distal end by the bent end, wherein the lead ribbon ring defines a horizontal plane, such that the lead ribbon ring is configured to engage a lumen of tissue and the at least one exposed electrode pad is oriented radially outward from the horizontal plane and is in electrical contact with the tissue;

bending the lead ribbon substrate;

inserting the bent end of the lead ribbon substrate at the catheter proximal end towards the catheter distal end;

advancing the bent end of lead ribbon substrate towards the catheter distal end; and sliding the bent end of the lead ribbon substrate out of an opening at the catheter distal end to effectuate the lead ribbon ring.

20. The method of claim 19, wherein the lead ribbon substrate further comprises a plurality of fixation members extending in the horizontal plane perpendicular to an exposed surface of the at least one exposed electrode pad, wherein sliding the bent end of the lead ribbon substrate out of the opening at the catheter distal end causes the plurality of fixation members to extend radially outward from the lead ribbon substrate to engage the surrounding tissue.

* * * * *